United States Patent

Kelly et al.

[11] Patent Number: 5,411,676
[45] Date of Patent: May 2, 1995

[54] CHIRAL DOPANTS FOR LIQUID CRYSTALLINE MIXTURES

[75] Inventors: Stephen Kelly, Möhlin, Switzerland; Frans Leenhouts, Achel, Belgium

[73] Assignee: Hoffmann-La Roche Inc., Nutley, N.J.

[21] Appl. No.: 304,601

[22] Filed: Sep. 12, 1994

Related U.S. Application Data

[60] Continuation of Ser. No. 796,518, Nov. 21, 1991, abandoned, which is a division of Ser. No. 570,677, Aug. 22, 1990, Pat. No. 5,093,027.

[30] Foreign Application Priority Data

Sep. 1, 1989 [CH] Switzerland ................ 3169/89

[51] Int. Cl.[6] .............. C09K 19/30; C09K 19/52; C09K 19/06; C07C 69/76
[52] U.S. Cl. .......... 252/299.630; 252/299.01; 252/299.6; 560/76
[58] Field of Search ........... 252/299.6, 299.63, 299.01; 560/76

[56] References Cited

U.S. PATENT DOCUMENTS

| | | | |
|---|---|---|---|
| 4,264,148 | 4/1981 | Gobl-Wunsch et al. | 359/92 X |
| 4,650,600 | 3/1987 | Heppke et al. | 252/299.01 |
| 4,826,620 | 5/1989 | Heppke et al. | 252/299.61 |
| 4,886,619 | 12/1989 | Janulis | 252/299.01 |
| 4,988,458 | 1/1991 | Heppke et al. | 252/299.63 |
| 5,043,094 | 8/1991 | Takano et al. | 252/299.61 |

FOREIGN PATENT DOCUMENTS

| | | |
|---|---|---|
| 2827471 | 6/1978 | Germany . |
| 3333677 | 9/1983 | Germany . |
| 3633967 | 10/1986 | Germany . |
| 3534777 | 4/1987 | Germany . |
| 3534780 | 4/1987 | Germany . |

OTHER PUBLICATIONS

Heppke et al., "Chiral Dotierstoffe", Handout at 15th Symposium on Liquid Crystals in Freiburg, Germany (1986).
Derwent Abstract of 3 534 777 No. 87-094723/14.
Derwent Abstract of DE 3,633,967.

*Primary Examiner*—C. Harris
*Attorney, Agent, or Firm*—George M. Gould; George W. Johnston

[57] ABSTRACT

Optically active dopants of the formula

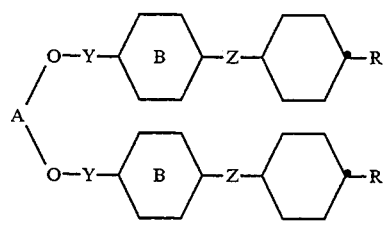

wherein A represents an optically active group selected from 1,1'-binaphthyl-2,2'-diyl, —CHR$^1$—CHR$^2$— or —CH(COOR$_3$)—CH(COOR$_4$)—; Z denotes a group —(CH$_2$)$_4$—, —O(CH$_2$)$_3$— or the trans form of —OCH$_2$—CH=CH—; R is hydrogen, methyl, phenyl or cyclohexyl; R$^2$ is methyl, phenyl or cyclohexyl; R$^3$ and R$^4$ denote alkyl; Y stands for —CO— or —CH$_2$—; ring B represents 1,4-phenytene or trans-1,4-cyclohexylene; and R is hydrogen, alkyl, alkoxy or cyano, liquid crystalline mixtures which contain such dopants and their use for optical and electro-optical purposes.

4 Claims, No Drawings

CHIRAL DOPANTS FOR LIQUID CRYSTALLINE MIXTURES

This is a continuation of U.S. application Ser. No. 07/796,518, filed Nov. 21, 1991, now abandoned which is a divisional application of U.S. application Ser. No. 07/570,677, filed Aug. 22, 1990, U.S. Pat. No. 5,093,027.

FIELD OF THE INVENTION

The present invention is concerned with novel chiral dopants for liquid crystals and their manufacture as well as liquid crystalline mixtures which contain such dopants and their use for optical and electro-optical purposes.

BACKGROUND OF THE INVENTION

Liquid crystal materials for electro-optical indicating devices frequently contain one or more optically active additives for the induction of a chiral structure. For example, for use in indicating devices having a twisted nematic structure a nematic liquid is preferably doped with an optically active additive, e.g. in order to avoid a reversal of the twisting direction (reverse twist) in TN cells (twisted-nematic) or in order to achieve an adequate twisting in cells having a highly twisted nematic structure such as STN cells (super twisted-nematic), SBE cells (super birefringence effect) or OMI cells (optical mode interference). Further, cholesteric liquid crystals for phase-change cells can preferably consist of a nematic basic material and one or more optically active dopants and ferroelectric liquid crystals for indicating devices based on chiral tilted smectic phases can preferably consist of a material having a tilted smectic phase and one or more optically active dopants.

The electro-optical characteristics of liquid crystal indicating devices are temperature-dependent, which is especially troublesome in the case of multiplex operation. It is, however, known that this temperature dependence can be compensated at least partially by adding chiral dopants which induce a decreasing pitch with increasing temperature. Such an inverse temperature dependence has been found only for a few compounds. It can, however, also be achieved by using at least two chiral dopants which have a different relative temperature dependence and which induce a different twisting direction as described in U.S. Pat. No. 4,264,148 corresponding to DE-A-2827471. Of course, this usually requires a relatively high amount of chiral dopants.

Cholesteric liquid crystals reflect light essentially only in a wavelength range for which the wavelength is about the same as the helical pitch. The spectral width of this reflection light can be varied by suitable choice of the liquid crystal. The reflected light is completely circularly polarized. The direction of rotation of the reflected light depends on the direction of rotation of the cholesteric helical structure. The opposite circularly polarized light is transmitted unimpaired. These properties can be employed for the production of optical filters, polarizers, analyzers etc. Further, cholesteric liquid crystals have also variously been used for thermochromic applications and in cosmetic preparations.

Cholesteric liquid crystals for the above applications preferably consist of a nematic or cholesteric basic material and one or more chiral dopants, which permits a simple adjustment of the desired helical pitch.

In order to achieve cholesteric mixtures having a pitch in the range of the wavelength of visible light, the chiral dopants should have a twisting capacity which is as high as possible and should have a good solubility in usual liquid crystal materials. Furthermore, the chiral dopants should have an adequate stability, should have a good compatibility with the mesophase type of the liquid crystal material and should not restrict the mesophase range too strongly. Such properties would also be desirable for chiral dopants for producing the twisted nematic structures referred to earlier, since their amount can be held low in order that the properties of the liquid crystal material are influenced only immaterially.

DETAILED DESCRIPTION OF THE INVENTION

The invention is concerned with optically active compounds of formula

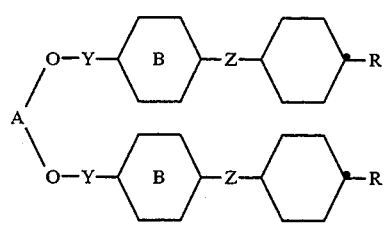

wherein A represents an optically active group selected from 1,1'-binaphthyl-2,2'-diyl, —CH-$R^1$—CHR$^2$— or —CH(COOR$^3$)—CH(COOR$^4$)—; Z is a group —(CH$_2$)$_4$—, —O(CH$_2$)$_3$— or the trans form of —OCH$_2$—CH=CH—; is hydrogen, methyl, phenyl or cyclohexyl; $R^2$ is methyl, phenyl or cyclohexyl; $R^3$ and $R^4$ are alkyl; Y is —CO— or —CH$_2$—; ring B represents 1,4-phenylene or trans-1,4-cyclohexylene; and R is hydrogen, alkyl, alkoxy or cyano.

The compounds of formula I are characterized by a good solubility and a high twisting capacity in usual liquid crystal materials. The groups —O—Y— and especially the bridging groups Z, which have 4 chain atoms, confer a high flexibility to the cyclic residues attached to the optically active group A. Surprisingly, this high flexibility does not, however, lead to stronger clearing point depression, i.e. the mesophase region of the liquid crystal material is not restricted or is restricted only comparatively little by the addition of chiral dopants of formula I. Moreover, the compounds of formula I can be manufactured readily and have adequate stability against chemical influences and against electric and magnetic fields. They therefore fulfil in an optimum manner the requirements referred to above.

The above terms "alkyl" and "alkoxy" denote in the scope of the present invention straight-chain or branched residues with preferably a maximum of 12 carbon atoms such as methyl, ethyl, propyl, butyl, isobutyl, 2-methylbutyl, pentyl, 3-methylpentyl, hexyl, heptyl, octyl, nonyl, decyl, undecyl, dodecyl, methoxy, ethoxy, propyloxy, butyloxy, isobutyloxy, 2-methylbutyloxy, pentyloxy, 3-methylpentyloxy, hexyloxy, heptyloxy, octyloxy, nonyloxy, decyloxy, undecyloxy, dodecyloxy and the like. Straight-chain residues are generally preferred. Preferred alkyl and alkoxy residues R are $C_1$-$C_{12}$-alkyl and $C_1$-$C_{12}$-alkoxy, especially $C_1$-$C_7$-alkyl and $C_1$-$C_7$-alkoxy. Preferred alkyl residues $R^3$ and $R^4$ are $C_1$-$C_7$-alkyl, especially $C_1$-$C_4$-alkyl such as methyl, ethyl, propyl and butyl.

The optically active groups A denote the diradical (after cleavage of the hydroxy groups) of an optically active diol HO—A—OH. Group A embraces especially the (R)-form and the (S)-form of 1,1'-binaphthyl-2,2'-diyl and of —CHR$^1$—CHR$^2$—, wherein R$^1$ is hydrogen, as well as the (R,R)-form and the (S,S)-form of —CH(COOR$^3$)—CH(COOR$^4$)— and of —CHR$^1$—CHR$^2$—, wherein R$^1$ is different from hydrogen.

Depending on the significance of the optically active group A and, respectively, the bridging group Z, formula I embraces optically active compounds of the following formulas

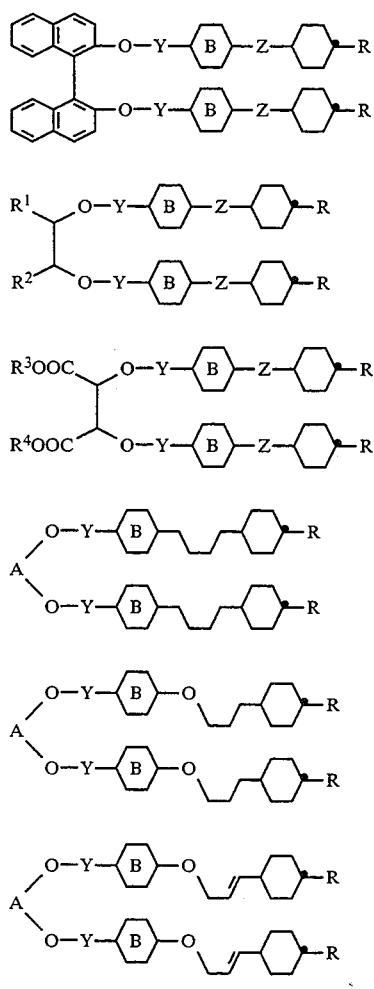

wherein A, R, R$^1$, R$^2$, R$^3$, R$^4$, Y, Z and ring B have the above significances.

In the above formulas R$^1$ preferably stands for hydrogen or for the same residue as R$^2$.

R$^3$ and R$^4$ can have the same significance or different significances and preferably denote $C_1$-$C_7$-alkyl, especially $C_1$-$C_4$-alkyl. Preferably, R$^3$ and R$^4$ have the same significance.

Examples of preferred optically active groups A are (R)-1,1'-binaphthyl-2,2'-diyl, (R)-1,2-propylene, (R)-1-phenyl-1,2-ethylene, (R)-1-cyclohexyl-1,2-ethylene, (2R,3R)-2,3-butylene, (1R,2R)-1,2-diphenyl-1,2-ethylene and the mirror image of these groups [i.e. the corresponding (S)- and, respectively, (S,S)-form].

Further preferred groups A are the (S,S)-form and the (R,R)-form of —CH(COOR$^3$)—CH(COOR$^4$)—, wherein R$^3$ and R$^4$ are $C_1$-$C_4$-alkyl.

In general there are preferred those compounds of the above formulas in which R is $C_1$-$C_{12}$-alkyl or cyano.

Preferably, ring B stands for 1,4-phenylene and/or Y stands for —CO—. In general there are especially preferred those compounds in which Z denotes —O(CH$_2$)$_3$—, Y denotes —CO— and ring B denotes 1,4-phenylene.

The compounds of formula I can be manufactured in accordance with the invention by a) for the manufacture of the compounds of formula I in which Y denotes —CO—, esterifying an optically active diol of the formula

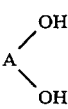      II wherein A has the significance given above, with a carboxylic acid of the formula

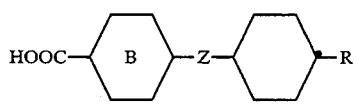      III wherein R, Z and ring B have the significances given above, or a suitable derivative thereof, or b) for the manufacture of the compounds of formula I in which Y denotes —CH$_2$—, etherifying an optically active diolate of the formula

      IV wherein A has the significance given above and M denotes an alkali metal, with a compound of the formula

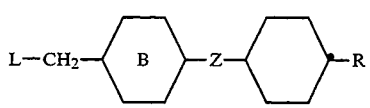      V wherein R, Z and ring B have the significances given above and L denotes a leaving group.

The esterification of a diol of formula II with a carboxylic acid of formula III or a suitable derivative (e.g. the acid chloride or anhydride) can be effected in a manner known per se. A preferred method is the reaction of the diol and the carboxylic acid in an inert organic solvent (e.g. in a halogenated hydrocarbon such as dichloromethane) in the presence of 4-(dimethylamino)pyridine and N,N'-dicyclohexylcarbodiimide.

The etherification of a diolate of formula IV with a compound of formula V can also be effected in a manner known per se, for example by reaction in an inert organic solvent such as toluene, benzene, hexane and the like at an elevated temperature. M preferably denotes lithium, sodium or potassium, especially sodium. The diolate can be obtained in a known manner from the diol of formula II, e.g. by reaction with the respective alkali metal or alkali metal hydride. L is a leaving group which is usual in $S_N2$ reactions, for example halogen such as chlorine, bromine or iodine, a sulphonyloxy group such as p-toluenesulphonyloxy and the like.

The optically active diols of formula II are known or are analogues of known compounds. Moreover, many of these diols are commercially available. The preparation of the compounds of formulas III and V can be effected according to known methods, for example according to the procedures illustrated in the working Examples.

The invention is also concerned with a liquid crystalline mixture containing a liquid crystalline carrier material and one or more optically active compounds of formula I. Suitable carrier materials are basically all liquid crystal materials which have a twistable liquid crystal phase with an adequate mesophase range. The compounds of formula I are especially suitable as chiral dopants for nematic or cholesteric carrier materials. The liquid crystalline carrier material can be a single compound or a mixture and preferably has a clearing point of at least about 60° C., particularly at least about 80° C. The amount of chiral dopant of formula I is determined essentially by its twisting capacity and the desired pitch. The amount of chiral dopant can therefore, depending on the application, vary in a wide range and can be, for example, about 0.1–30 wt. %. For indicating devices based on liquid crystals having a twisted nematic structure a pitch of about 3–40 m is usually required depending on the type of cell and thickness of cell and therefore a correspondingly smaller amount is sufficient. On the other hand, for applications which are based on the reflection of visible light by cholesteric layers, pitches of about 0.4–0.6 m are required, which necessitates a correspondingly higher amount of chiral dopant. Suitable liquid crystalline carrier materials are known in large numbers and are commercially available. As a rule, liquid crystalline mixtures containing two or more components are preferred as carrier materials. Basically, however, one liquid crystalline compound can be used as the carrier material when it has a sufficiently broad mesophase.

Compounds of the following formulas are especially suitable as components for liquid crystalline carrier materials

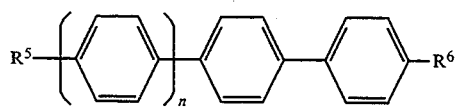

VI

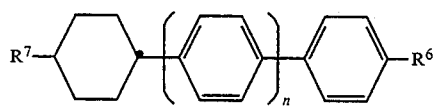

VII

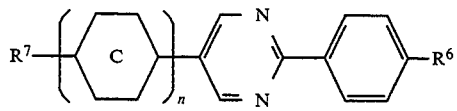

VIII

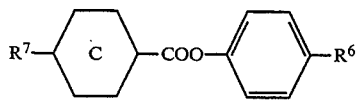

IX

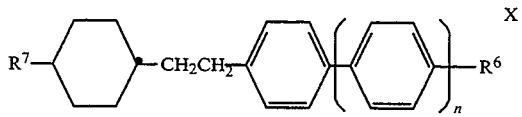

X

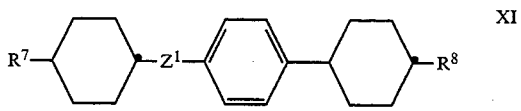

XI

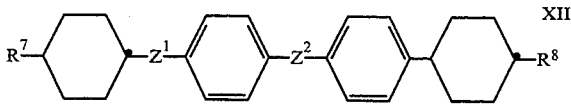

XII

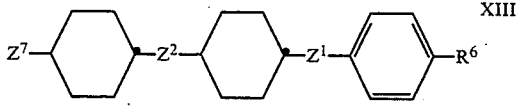

XIII wherein n stands for the number 0 or 1; $R^5$ denotes alkyl, alkoxy, alkenyl or alkenyloxy; $R^6$ is cyano, alkyl, alkoxy, alkenyl or alkenyloxy; $R^7$ and $R^8$ each independently denote alkyl or alkenyl; ring C represents 1,4-phenylene or trans-1,4-cyclohexylene; $Z^1$ denotes a single covalent bond, —COO— or —CH$_2$CH$_2$—; and $Z^2$ is a single covalent bond or —CH$_2$CH$_2$—.

$R^5$, $R^6$, $R^7$ and $R^8$ each preferably have a maximum of 12 carbon atoms, particularly a maximum of 7 carbon atoms. Preferred alkenyl groups are 1E-alkenyl, 3E-alkenyl and 4Z-alkenyl. Preferred alkenyloxy groups are 2E-alkenyloxy and 3Z-alkenyloxy.

The invention is illustrated in more detail by the following Examples. In connection with liquid crystal phases and phase transitions, C is a crystalline phase, N is a nematic phase, N* is a cholesteric phase and I is the isotropic phase. The helical pitch is denoted by p. Optical antipodes have in each case "mirror image properties", i.e. the same melting point etc., but lead to an opposite helical direction of rotation and an opposite circular polarization of the reflected light.

Example 1

0.5 g of 4-[4-(trans-4-pentylcyclohexyl)-1-butyl]benzoic acid, 0.1 g of R(+)-1,1'-bi-2-naphthol and 0.04 g of 4-(dimethylamino)pyridine were dissolved in 50 ml of dichloromethane and the solution was treated portionwise with 0.3 g of N,N'-dicyclohexylcarbodiimide within 10 minutes while stirring. The mixture was stirred at room temperature overnight and then filtered. The filtrate was diluted with dichloromethane, washed twice with 50 ml of saturated sodium carbonate solution each time and then with water, dried over magnesium sulphate, filtered and subsequently concentrated. The crude product obtained was purified by chromatography on silica gel with toluene. Recrystallization from ethanol gave (R)-2,2'-bis-[4-[4-(trans-4-pentylcyclohexyl)-1-butyl]benzoyloxy]-1,1'-binaphthyl as an oil (m.p. <25° C.).

The 4-[4-(trans-4-pentylcyclohexyl)-1-butyl]benzoic acid used as the starting material was prepared as follows:

(a) A mixture of 20 g of 3-(trans-4-pentylcyclohexyl)-1-propanal, 66 g of 4-cyanobenzyl-triphenylphosphonium bromide and 500 ml of t-butyl methyl ether was treated with 16 g of potassium t-butylate while gassing with argon at 0° C. The reaction mixture was stirred at room temperature for 2 hours and then treated with water. The reaction mixture was extracted three times with 50 ml of diethyl ether each time. The combined organic phases were washed with water, dried over magnesium sulphate, filtered and subsequently concentrated. The residue was treated several times with hexane. The combined organic phases were concentrated several times. The crude product obtained was purified by chromatography on silica gel with hexane. This gave 40 g of 4-[4-(trans-4-pentylcyclohexyl)-1-butenyl]benzonitrile (cis-/trans mixture).

(b) A mixture of 40 g of 4-[4-(trans-4-pentylcyclohexyl)-1-butenyl]benzonitrile, 2 g of palladium/carbon (5%) and 250 ml of ethyl acetate was stirred while gassing with hydrogen. Subsequently, the inorganic material was filtered off and the filtrate was concentrated. The residue was purified by chromatography on silica gel with toluene/ethyl acetate (vol. 9:1). Recrystallization from ethanol gave 36 g of pure 4-[4-(trans-4-pentylcyclohexyl)-1-butyl]benzonitrile with m.p. 51° C.

(c) A mixture of 36 g of 4-[4-(trans-4-pentylcyclohexyl)-1-butyl]benzonitrile, 300 ml of concentrated sulphuric acid, 300 ml of glacial acetic acid and 300 ml of water was heated to a temperature of 120° C. overnight. The cooled reaction mixture was poured into ice-water and the white precipitate was filtered off. The filter residue was washed with water and subsequently recrystallized from ethanol. This gave 28 g of 4-[4-(trans-4-pentylcyclohexyl)-1-butyl]benzoic acid with m.p. (C-N) 195° C. and cl.p. (N-I) 199° C.

The following compounds can be manufactured in an analogous manner:

(R)-2,2'-Bis-[4-[4-(trans-4-propylcyclohexyl)-1-butyl]benzoyloxy]-1,1'-binaphthyl;
(R)-2,2'-bis-[4-[4-(trans-4-heptylcyclohexyl)-1-butyl]benzoyloxy]-1,1'-binaphthyl;
(R)-1,2-bis-[4-[4-(trans-4-propylcyclohexyl)-1-butyl]benzoyloxy]-1-phenylethane;
(R)-1,2-bis-[4-[4-(trans-4-pentylcyclohexyl)-1-butyl]benzoyloxy]-1-phenylethane, m.p. 103° C.;
(R)-1,2-bis-[4-[4-(trans-4-heptylcyclohexyl)-1-butyl]benzoyloxy]-1-phenylethane;
(R)-1,2-bis-[4-[4-(trans-4-propylcyclohexyl)-1-butyl]benzoyloxy]propane;
(R)-1,2-bis-[4 -[4-(trans-4-pentylcyclohexyl)-1-butyl]benzoyloxy]propane;
(R)-1,2-bis-[4 -[4-(trans-4-heptylcyclohexyl)-1-butyl]benzoyloxy]propane;
(2R,3R)-2,3-bis-[4-[4-(trans-4-propylcyclohexyl)-1-butyl]benzoyloxy]butane;
(2R,3R)-2,3-bis-[4-[4-(trans-4-pentylcyclohexyl)-1-butyl]benzoyloxy]butane;
(2R,3R)-2,3-bis-[4-[4-(trans-4-heptylcyclohexyl)-1-butyl]benzoyloxy]butane;
(1R,2R)-1,2-bis-[4-[4-(trans-4-propylcyclohexyl)-1-butyl]benzoyloxy]-1,2-diphenylethane;
(1R,2R)-1,2-bis-[4-[4-(trans-4-pentylcyclohexyl)-1-butyl]benzoyloxy]-1,2-diphenylethane;
(1R,2R)-1,2-bis-[4-[4-(trans-4-heptylcyclohexyl)-1-butyl]benzoyloxy]-1,2-diphenylethane;
dimethyl (2R,3R)-2,3-bis-[4-[4-(trans-4-pentylcyclohexyl)-1-butyl]benzoyloxy]butanedioate;
diethyl (2R,3R)-2,3-bis-[4-[4-(trans-4-pentylcyclohexyl)-1-butyl]benzoyloxy]butanedioate;
dipropyl (2R,3R)-2,3-bis-[4-[4-(trans-4-pentylcyclohexyl)-1-butyl]benzoyloxy]butanedioate;
dibutyl (2R,3R)-2,3-bis-[4-[4-(trans-4-pentylcyclohexyl)-1-butyl]benzoyloxy]butanedioate;

as well as the optical antipodes of the named compounds.

Example 2

2.0 g of R(+)-1,1'-bi-2-naphthol, 5.0 g of 4-[3-(trans-4-pentylcyclohexyl)-1-propyloxy]benzoic acid, 3.0 g of N,N'-dicyclohexylcarbodiimide, 0.1 g of 4-(dimethylamino)pyridine and 500 ml of dichloromethane were reacted in an analogous manner to Example 1 to give 6.5 g of (R)-2,2'-bis-[4-[3-(trans-4-pentylcyclohexyl)-1-propyloxy]benzoyloxy]-1,1'-binaphthyl with m.p. 50° C.

The 4-[3-(trans-4-pentylcyclohexyl)-1-propyloxy]benzoic acid used as the starting material was prepared as follows:

(a) A mixture of 1.9 g of 4-hydroxybenzaldehyde, 5.0 g of 3-(trans-4-pentylcyclohexyl)-1-propyl bromide, 8.3 g of potassium carbonate and 50 ml of butanone was heated under reflux overnight. Subsequently, the cooled reaction mixture was poured into water and extracted three times with 50 ml of diethyl ether each time. The combined organic phases were washed with 500 ml of water, dried over magnesium sulphate, filtered and concentrated. Chromatography of the residue on silica gel with toluene and recrystallization from ethanol gave 6.0 g of pure 4-[3-(trans-4-pentylcyclohexyl)-1-propyloxy]benzaldehyde.

(b) A solution of 5 g of 4-[3-(trans-4-pentylcyclohexyl)-1-propyloxy]benzaldehyde in 100 ml of acetone was treated dropwise with 10 ml of Jones' reagent. The mixture was stirred at room temperature for 1 hour and then poured into 100 ml of water. The precipitate which thereby resulted was filtered off, washed portionwise with water and dried in a vacuum. The crude product was recrystallized from ethanol and gave 2.2 g of pure 4-[3-(trans-4-pentylcyclohexyl)-1-propyloxy]benzoic acid with m.p. (C-N) 204° C. and cl.p. (N-I) 215° C.

The following compounds can be manufactured in an analogous manner:

(R)-2,2'-Bis-[4-[3-(trans-4-propylcyclohexyl)-1-propyloxy]-benzoyloxy]-1,1'-binaphthyl;
(R)-2,2'-bis-[4-[3-(trans-4-heptylcyclohexyl)-1-propyloxy]-benzoyloxy]-1,1'-binaphthyl;
(2R,3R)-2,3-bis-[4-[3-(trans-4-propylcyclohexyl)-1-propyloxy]benzoyloxy]butane;
(2R,3R )-2,3-bis-[4 -[3-(trans-4-pentylcyclohexyl)-1-propyloxy]benzoyloxy]butane, m.p. 109° C.;
(2R,3R )-2,3-bis-[4 -[3-(trans-4-heptylcyclohexyl)-1-propyloxy]benzoyloxy]butane;
(1R,2R )-1,2-bis-[4 -[3-(trans-4-propylcyclohexyl)-1-propyloxy]benzoyloxy]-1,2-diphenylethane;
(1R,2R )-1, 2-bis-[4-[3-(trans-4-pentylcyclohexyl)-1-propyloxy]benzoyloxy]-1,2-diphenylethane, m.p. 75° C.;

(1R,2R)-1,2-bis-[4-[3-(trans-4-heptylcyclohexyl)-1-propyloxy]benzoyloxy]-1,2-diphenylethane;
(R)-1,2-bis-[4-[3-(trans-4-propylcyclohexyl)-1-propyloxy]benzoyloxy]-1-phenylethane;
(R)-1,2-bis-[4-[3-(trans-4-pentylcyclohexyl)-1-propyloxy]benzoyloxy]-1-phenylethane, m.p. 115° C.;
(R)-1,2-bis-[4-[3-(trans-4-heptylcyclohexyl)-1-propyloxy]benzoyloxy]-1-phenylethane;
(R)-1,2-bis-[4-[3-(trans-4-propylcyclohexyl)-1-propyloxy]benzoyloxy]propane;
(R)-1,2-bis-[4-[3-(trans-4-pentylcyclohexyl)-1-propyloxy]benzoyloxy]propane;
(R)-1,2-bis-[4-[3-(trans-4-heptylcyclohexyl)-1-propyloxy-benzoyloxy]propane;
dimethyl (2R,3R)-2,3-bis-[4-[3-(trans-4-pentylcyclohexyl)-1-propyloxy]benzoyloxy]butanedioate;
diethyl (2R,3R)-2,3-bis-[4-[3-(trans-4-pentylcyclohexyl)-1-propyloxy]benzoyloxy]butanedioate, m.p. 59° C.;
dipropyl (2R,3R)-2,3-bis-[4-[3-(trans-4-pentylcyclohexyl)-1-propyloxy]benzoyloxy]butanedioate;
dibutyl (2R,3R)-2,3-bis-[4-[3-(trans-4-pentylcyclohexyl)-1-propyloxy]benzoyloxy]butanedioate, m.p. 66° C.;

as well as the optical antipodes of the named compounds.

Example 3

1.0 g of R(+)-1,1'-bi-2-naphthol, 2.5 g of 4-[(E)-3-(trans-4-pentylcyclohexyl)allyloxy]benzoic acid, 1.3 g of N,N'-dicyclohexylcarbodiimide, 0.04 g of 4-(dimethylamino)pyridine and 250 ml of dichloromethane were reacted in an analogous manner to Example 1 to give 2.2 g of (R)-2,2'-bis-[4-[(E)-3-(trans-4-pentylcyclohexyl)allyloxy]benzoyloxy]-1,1'-binaphthyl with m.p. 93° C.

The 4-[(E)-3-(trans-4-pentylcyclohexyl)allyloxy]benzoic acid used as the starting material was prepared as follows:

(a) A solution of 13.5 g of ethyl (E)-3-(trans-4-pentylcyclohexyl)acrylate in 100 ml of dichloromethane was treated dropwise at −78° C. and while gassing with nitrogen with a 20% solution of diisobutylaluminium hydride in hexane. After completion of the addition the slightly yellow solution was stirred for a further 1 hour and then treated cautiously with 10 ml of 25% hydrochloric acid. The reaction mixture was poured into 100 ml of water and the organic phase was separated. The aqueous phase was back-extracted twice with 100 ml of dichloromethane each time. The combined organic phases were washed with 500 ml of water, 500 ml of concentrated potassium hydrogen carbonate solution and again with 500 ml of water and subsequently dried over magnesium sulphate, filtered and concentrated. Distillation of the residue gave 10 g of (E)-3-(trans-4-pentylcyclohexyl)allyl alcohol with b.p. 174°–175° C./15 mmHg.

(b) A mixture of 5.0 g of (E)-3-(trans-4-pentylcyclohexyl)allyl alcohol, 2.9 g of 4-hydroxybenzaldehyde, 4.1 g of diethyl azodicarboxylate, 6.2 g of triphenylphosphine and 100 ml of tetrahydrofuran was stirred at room temperature overnight and then concentrated. The residue was suspended in 300 ml of hexane, filtered and again concentrated. Chromatography of the residue on silica gel with toluene and recrystallization from hexane gave 4.5 g of pure 4-[(E)-3-(trans-4-pentylcyclohexyl)allyloxy]benzaldehyde with m.p. 55° C.

(c) 4.0 g of 4-[(E)-3-(trans-4-pentylcyclohexyl)allyloxy]benzaldehyde, 10 ml of Jones' reagent and 100 ml of acetone were reacted in an analogous manner to Example 2(b) to give 2.6 g of 4-[(E)-3-(trans-4-pentylcyclohexyl)allyloxy]benzoic acid with m.p. 215° C.

The following compounds can be manufactured in an analogous manner:

(2R,3R)-2,3-Bis-[4-[(E)-3-(trans-4-propylcyclohexyl)allyloxy]benzoyloxy]butane;
(2R,3R)-2,3-bis-[4-[(E)-3-(trans-4-pentylcyclohexyl)allyloxy]benzoyloxy]butane;
(2R,3R)-2,3-bis-[4-[(E)-3-(trans-4-heptylcyclohexyl)allyloxy]benzoyloxy]butane;
(1R,2R)-1,2-bis-[4-[(E)-3-(trans-4-propylcyclohexyl)allyloxy]benzoyloxy]-1,2-diphenylethane;
(1R,2R)-1,2-bis-[4-[(E)-3-(trans-4-pentylcyclohexyl)allyloxy]benzoyloxy]-1,2-diphenylethane;
(1R,2R)-1,2-bis-[4-[(E)-3-(trans-4-heptylcyclohexyl)allyoxy]benzoyloxy]1,2-diphenylethane;
(R)-1,2-bis-[4-[(E)-3-(trans-4-propylcyclohexyl)allyloxy]benzoyloxy]-1-phenylethane;
(R)-1,2-bis-[4-[(E)-3-(trans-4-pentylcyclohexyl)allyloxy]benzoyloxy]-1-phenylethane, m.p. 101° C.;
(R)-1,2-bis-[4-[(E)-3-(trans-4-heptylcyclohexyl)allyloxy]benzoyloxy]-1-phenylethane;
(R)-1,2-bis-[4-[(E)-3-(trans-4-propylcyclohexyl)allyloxy]benzoyloxy]propane;
(R)-1,2-bis-[4-[(E)-3-(trans-4-pentylcyclohexyl)allyloxy]benzoyloxy]propane;
(R)-1,2-bis-[4-[(E)-3-(trans-4-heptylcyclohexyl)allyloxy]benzoyloxy]propane;
dimethyl (2R,3R)-2,3-bis-[4-[(E)-3-(trans-4-pentylcyclohexyl)allyloxy]benzoyloxy]butanedioate;
diethyl (2R,3R)-2,3-bis-[4-[(E)-3-(trans-4-pentylcyclohexyl)allyloxy]benzoyloxy]butanedioate;
dipropyl (2R,3R)-2,3-bis-[4-[(E)-3-(trans-4-pentylcyclohexyl)allyloxy]benzoyloxy]butanedioate;
dibutyl (2R,3R)-2,3-bis-[4-[(E)-3-(trans-4-pentylcyclohexyl)allyloxy]benzoyloxy]butanedioate;

as well as the optical antipodes of the named compounds.

Example 4

0.5 g of sodium R(−)-1-phenyl-1,2-ethanediolate, 2 g of 4-[4-(trans-4-pentylcyclohexyl)-1-butyl]benzyl p-toluenesulphonate and 100 ml of toluene were heated under reflux for 48 hours and then filtered. The filtrate was concentrated and the residue was purified by chromatography on silica gel with toluene. Recrystallization from ethanol gave (R)-1,2-bis-[4-[4-(trans-4-pentylcyclohexyl)-1-butyl]benzyloxy]-1-phenylethane.

The 4-[4-(trans-4-pentylcyclohexyl)-1-butyl]benzyl p-toluenesulphonate used as the starting material was prepared as follows:

(a) 3.8 g of lithium aluminium hydride were placed in 100 ml of absolute tetrahydrofuran while gassing with argon and treated within 30 minutes with a solution of 10 g of 4-[4-(trans-4-pentylcyclohexyl)-1-butyl]benzoic acid in 100 ml of absolute tetrahydrofuran. After completion of the addition the reaction mixture was heated to reflux for 1 hour, then poured cautiously into 200 ml of 2N hydrochloric acid and extracted three times with 100 ml of diethyl ether each time. The organic phases were washed with 100 ml of saturated sodium carbonate solution, dried over magnesium sulphate and concentrated. This gave 9.2 g of 4-[4-(trans-4-pentylcyclohexyl)-1-butyl]benzyl alcohol.

(b) A solution of 9 g of 4-[4-(trans-4-pentylcyclohexyl)-1-butyl]benzyl alcohol in 50 ml of pyridine was treated portionwise with 10 g of p-tosyl chloride at room temperature and while gassing with argon. After stirring at room temperature for 24 hours (formation of a white precipitate) the reaction mixture, cooled to 0° C., was treated with 20 ml of water (slightly exothermic), made acid (pH 1) with 50 ml of 25% hydrochloric acid and extracted three times with 100 ml of diethyl ether each time. The combined organic phases were washed with 500 ml of water, 500 ml of dilute sodium carbonate solution and again with 500 ml of water and then subsequently dried over magnesium sulphate and concentrated. This gave 15 g of 4-[4-(trans-4-pentylcyclohexyl)-1-butyl]benzyl p-toluenesulphonate.

The following compounds can be manufactured in an analogous manner:

(R)-1,2-Bis-[4-[4-(trans-4-propylcyclohexyl)-1-butyl]-benzyloxy]-1-phenylethane;
(R)-1,2-bis-[4-[4-(trans-4-heptylcyclohexyl)-1-butyl]-benzyloxy]-1-phenylethane;
(R) 1,2-bis-[4-[4-(trans-4-propylcyclohexyl)-1-butyl]-benzyloxy]propane;
(R)-1,2-bis-[4-[4-(trans-4-pentylcyclohexyl)-1-butyl]-benzyloxy]propane;
(R)-1,2-bis-[4-[4-(trans-4-heptylcyclohexyl)-1-butyl]-benzyloxy]propane;
(2R,3R)-2,3-bis-[4-[4-(trans-4-propylcyclohexyl)-1-butyl]benzyloxy]butane;
(2R,3R)-2,3-bis-[4-[4-(trans-4-pentylcyclohexyl)-1-butyl]benzyloxy]butane;
(2R,3R)-2,3-bis-[4-[4-(trans-4-heptylcyclohexyl)-1-butyl]benzyloxy]butane;
(1R,2R)-1,2-bis-[4-[4-(trans-4-propylcyclohexyl)-1-butyl]benzyloxy]-1,2-diphenylethane;
(1R,2R)-1,2-bis-[4-[4-(trans-4-pentylcyclohexyl)-1-butyl]benzyloxy]-1,2-diphenylethane;
(1R,2R)-1,2-bis-[4-[4-(trans-4-heptylcyclohexyl)-1-butyl]benzyloxy]-1,2-diphenylethane;
(R)-2,2'-bis-[4-[4-(trans-4-propylcyclohexyl)-1-butyl]-benzyloxy]-1,1'-binaphthyl;
(R)-2,2'-bis-[4-[4-(trans-4-pentylcyclohexyl)-1-butyl]-benzyloxy]-1,1'-binaphthyl;
(R)-2,2'-bis-[4-[4-(trans-4-heptylcyclohexyl)-1-butyl]-benzyloxy]-1,1'-binaphthyl;
(2R,3R )-2,3-bis-[4-[3-(trans-4-propylcyclohexyl)-1-propyloxy]benzyloxy]butane;
(2R,3R )-2,3-bis-[4-[3-(trans-4-pentylcyclohexyl)-1-propyloxy]benzyloxy]butane;
(2R,3R)-2,3-bis-[4-[3-(trans-4-heptylcyclohexyl)-1-propyloxy]benzyloxy]butane;
(1R,2R)-1,2-bis-[4-[3-(trans-4-propylcyclohexyl)-1-propyloxy]benzyloxy]-1,2-diphenylethane;
(1R,2R)-1,2-bis-[4-[3-(trans-4-pentylcyclohexyl)-1-propyloxy]benzyloxy]-1,2-diphenylethane;
(1R,2R)-1,2-bis-[4-[3-(trans-4-heptylcyclohexyl)-1-propyloxy]benzyloxy]-1,2-diphenylethane;
(R)-1,2-bis-[4-[3-(trans-4-propylcyclohexyl)-1-propyloxy]benzyloxy]-1-phenylethane;
(R)-1,2-bis-[4-[3-(trans-4-pentylcyclohexyl)-1-propyloxy]benzyloxy]-1-phenylethane;
(R)-1,2-bis-[4-[3-(trans-4-heptylcyclohexyl)-1-propyloxy]benzyloxy]-1-phenylethane;
(R)-1,2-bis-[4-[3-(trans-4-propylcyclohexyl)-1-propyloxy]benzyloxy]propane;
(R)-1,2-bis-[4-[3-(trans-4-pentylcyclohexyl)-1-propyloxy]benzyloxy]propane;
(R)-1,2-bis-[4-[3-(trans-4-heptylcyclohexyl)-1-propyloxy]benzyloxy]propane;
(R)-2,2'-bis-[4-[3-(trans-4-propylcyclohexyl)-1-propyloxy]benzyloxy]-1,1'-binaphthyl;
(R)-2,2'-bis-[4-[3-(trans-4-pentylcyclohexyl)-1-propyloxy]benzyloxy]-1,1'-binaphthyl;
(R)-2,2'-bis-[4-[3-(trans-4-heptylcyclohexyl)-1-propyloxy]benzyloxy]-1,1'-binaphthyl;
dimethyl (2R,3R)-2,3-bis-[4-[4-(trans-4-pentylcyclohexyl)-1-butyl]benzyloxy]butanedioate;
diethyl (2R,3R)-2,3-bis-[4-[4-(trans-4-pentylcyclohexyl)-1-butyl]benzyloxy]butanedioate;
dipropyl (2R,3R)-2,3-bis-[4-[4-(trans-4-pentylcyclohexyl)-1-butyl]benzyloxy]butanedioate;
dibutyl (2R,3R)-2,3-bis-[4-[4-(trans-4-pentylcyclohexyl)-1-butyl]benzyloxy]butanedioate;
dimethyl (2R,3R)-2,3-bis-[4-[3-(trans-4-pentylcyclohexyl)-1-propyloxy]benzyloxy]butanedioate;
diethyl (2R,3R)-2,3-bis-[4-[3-(trans-4-pentylcyclohexyl)-1-propyloxy]benzyloxy]butanedioate;
dipropyl (2R,3R)-2,3-bis-[4-[3-(trans-4-pentylcyclohexyl)-1-propyloxy]benzyloxy]butanedioate;
dibutyl (2R,3R)-2,3-bis-[4-[3-(trans-4-pentylcyclohexyl)-1-propyloxy]benzyloxy]butanedioate;
dimethyl (2R,3R)-2,3-bis-[4-[(E)-3-(trans-4-pentylcyclohexyl)allyloxy]benzyloxy]butanedioate;
diethyl (2R,3R)-2,3-bis-[4-[(E)-3-(trans-4-pentylcyclohexyl)allyloxy]benzyloxy]butanedioate;
dipropyl (2R,3R)-2,3-bis-[4-[(E)-3-(trans-4-pentylcyclohexyl)allyloxy]benzyloxy]butanedioate;
dibutyl (2R,3R)-2,3-bis-[4-[(E)-3-(trans-4-pentylcyclohexyl)allyloxy]benzyloxy]butanedioate;

as well as the optical antipodes of the named compounds.

Example 5

The following liquid crystal basic mixture BM-1 was used to measure the induced pitch and its temperature dependence in liquid crystal materials.

5.36 wt. % of 4'-ethyl-4-cyanobiphenyl,
3.18 wt. % of 4'-propyl-4-cyanobiphenyl,
6.08 wt. % of 4'-butyl-4-cyanobiphenyl,
6.53 wt. % of 4-(trans-4-propylcyclohexyl)benzonitrile,
14.67 wt. % of 4-(trans-4-pentylcyclohexyl)benzonitrile,
5.21 wt. % of 4-ethyl-1-(trans-4-propylcyclohexyl)benzene,
16.54 wt. % of 4-ethoxy-1-[2-(trans-4-propylcyclohexyl)ethyl]benzene,
5.60 wt. % of 4''-pentyl-4-cyano-p-terphenyl,
5.71 wt. % of 4'-(trans-4-pentylcyclohexyl)-4-cyanobiphenyl,
15.95 wt. % of 1-[2-(trans-4-butylcyclohexyl)ethyl]-4-(trans-4-pentylcyclohexyl)benzene,
4.74 wt. % of 4-[2-(trans-4-butylcyclohexyl)ethyl]-4'-(trans-4-pentylcyclohexyl)biphenyl,
7.59 wt. % of 4-[2-(trans-4-butylcyclohexyl)ethyl]-4'-(trans-4-pentylcyclohexyl)-1,1'-ethylenedibenzene,
2.84 wt. % of trans-4-[2-(trans-4-propylcyclohexyl)ethyl]cyclohexanecarboxylic acid 4-cyanophenyl ester;

m.p. < −30° C., cl.p. (N-I) 90° C.; =8.5, n=0.139 and =22 mPa s measured at 22° C.

Liquid crystal basic mixture BM-1 was treated with each of the following optically active dopants:

D-1=(R)-2,2'-bis-[4-[3-(trans-4-pentylcyclohexyl)-1-propyloxy]benzoyloxyl-1,1'-binaphthyl,
D-2=(1R,2R)-1,2-bis-[4-[3-(trans-4-pentylcyclohexyl)-1-propyloxy]benzoyloxy]-1,2-diphenylethane,
D-3=(2R,3R)-2,3-bis-[4-[3-(trans-4-pentylcyclohexyl)-1-propyloxy]benzoyloxy]butane,
D-4=(R)-1,2-bis-[4-[3-(trans-4-pentylcyclohexyl)-1-propyloxy]benzoyloxy]-1-phenylethane.

The results compiled in Table 1 were obtained for the chiral doped mixtures, whereby A, B and C denote the parameters of the serial progression $$\frac{1}{pc} = A + BT_1 + CT_1^2$$

and p, c and $T_1$ have the following significances:
$T_1 = T-22°$ C.
T=temperature in °C.
p=pitch in m (a positive value is a clockwise helical structure and a negative value is an anticlockwise helical structure)
concentration of the optically active dopant in wt. %.

TABLE 1

| Mixture | Dopant | A $[10^{-2} \cdot \mu m^{-1} \cdot wt. \%^{-1}]$ | B $[10^{-4} \cdot \mu m^{-1} \cdot wt. \%^{-1} \cdot °C.^{-1}]$ | C $[10^{-6} \cdot \mu m^{-1} \cdot wt. \%^{-1} \cdot °C.^{-2}]$ | p · c (at 22°) [μm · wt. %] | p (at 22° C.) [μm] |
|---|---|---|---|---|---|---|
| M-1 | 0.5 wt. % D-1 | 55.42 | −11.4752 | −17.818 | 1.8 | 3.6 |
| M-2 | 0.3 wt. % D-2 | −35.73 | −5.2971 | 4.063 | −2.8 | −9.3 |
| M-3 | 3 wt. % D-3 | 4.465 | −3.705 | −4.487 | 22.4 | 7.5 |
| M-4 | 1 wt. % D-4 | 21.05 | −4.8410 | 8.080 | −4.8 | −4.8 |

Example 6

The mixtures M-5 and M-6 given in Table 2 illustrate cholesteric mixtures which selectively reflect light in the visible region. D-1 and D-4 denote the optically active dopants referred to in Example 5. The concentrations are given in wt. %.

TABLE 2

|  | M-5 | M-6 |
|---|---|---|
| 4'-Pentyl-4-cyanobiphenyl | 37.80% | 35.08% |
| 4'-Heptyl-4-cyanobiphenyl | 20.79% | 12.29% |
| 4'-Octyloxy-4-cyanobiphenyl | 13.23% | 12.28% |
| 4''-Pentyl-4-cyano-p-terphenyl | 6.62% | 6.14% |
| 4-[5-(4-Pentylphenyl)-2-pyrimidinyl]-benzonitrile | 4.72% | 4.39% |
| 4-[5-(trans-4-Ethylcyclohexyl)-2-pyrimidinyl]benzonitrile | 5.67% | 5.26% |
| 4-[5-(trans-4-Pentylcyclohexyl)-2-pyrimidinyl]benzonitrile | 5.67% | 5.26% |
| D-1 | 5.50% |  |
| D-4 |  | 12.30% |
| p (at 22° C.) | 470 nm | −550 nm |

We claim:
1. An optically active compound of formula

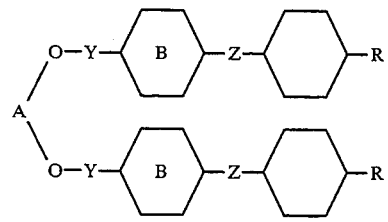

wherein:
A represents an optically active group selected from the group consisting of (R,R)—CH(COOR$^3$)—CH(COOR$^4$)—, or (S,S)—CH(COOR$^3$)—CH(COOR$^4$)—;
Z denotes a group —(CH$_2$)$_4$—, —O(CH$_2$)$_3$—, or the trans- form of —OCH$_2$—CH=CH—;
R$^3$ and R$^4$ are C$_1$-C$_4$-alkyl;
Y stands for —CO— or —CH$_2$—;
R is hydrogen, C$_1$-C$_{12}$-alkyl, C$_1$-C$_{12}$-alkoxy or cyano; and
ring B represents 1,4-phenylene or trans-1,4-cyclohexylene.

2. A compound according to claim 1 wherein R is C$_1$-C$_{12}$-alkyl or cyano.

3. A liquid crystalline mixture containing a liquid crystalline carrier material and one or more optically active compounds of formula

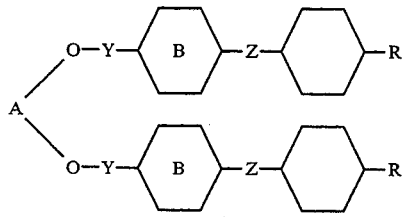

wherein
A represents an optically active group selected from the group consisting of (R,R)—CH(COOR$^3$)—CH(COOR$^4$)—, or (S,S)—CH(COOR$^3$)—CH(COOR$^4$)—;
Z denotes a group —(CH$_2$)$_4$—, —O(CH$_2$)$_3$—, or the trans- form of —OCH$_2$—CH=CH—;
R$^3$ and R$^4$ are C$_1$-C$_4$-alkyl;
Y stands for —CO— or —CH$_2$—;
R is hydrogen, C$_1$-C$_{12}$-alkyl, C$_1$-C$_{12}$-alkoxy or cyano; and
ring B represents 1,4-phenylene or trans-1,4-cyclohexylene.

4. In a ferroelectric electro-optical indicating device of the type having a liquid crystalline mixture sandwiched between two transparent plates having polarizers and electrode means, the improvement comprising said liquid crystalline mixture having an optically active compound of formula:

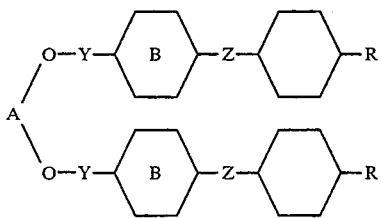

wherein
A represents an optically active group selected from the group consisting of (R,R)—CH(COOR$^3$)—CH(COOR$^4$)—, or (S,S)—CH(COOR$^3$)—CH(COOR$^4$)—;
Z denotes a group —(CH$_2$)$_4$—, —O(CH$_2$)$_3$—, or the trans- form of —OCH$_2$—CH=CH—;
R$^3$ and R$^4$ are C$_1$-C$_4$-alkyl;
Y stands for —CO— or —CH$_2$—;
R is hydrogen, C$_1$-C$_{12}$-alkyl, C$_1$-C$_{12}$-alkoxy or cyano; and
ring B represents 1,4-phenylene or trans-1,4-cyclohexylene.

* * * * *